US009872792B2

(12) United States Patent
Romo et al.

(10) Patent No.: US 9,872,792 B2
(45) Date of Patent: Jan. 23, 2018

(54) WRIST BRACE AND METHOD AND COMPONENTS FOR SECURING THE SAME

(71) Applicant: Ossur hf, Reykjavik (IS)

(72) Inventors: Harry Duane Romo, Aliso Viejo (CA); Concetta Maria Huffa, Encino, CA (US); Gil David Manalo, San Clemente, CA (US); Zachariah J. Klutts, Trabuco Canyon, CA (US)

(73) Assignee: OSSUR HF, Reykjavik (IS)

( * ) Notice: Subject to any disclaimer, the term of this patent is extended or adjusted under 35 U.S.C. 154(b) by 249 days.

(21) Appl. No.: 13/764,250

(22) Filed: Feb. 11, 2013

(65) Prior Publication Data

US 2013/0211304 A1 Aug. 15, 2013

Related U.S. Application Data

(60) Provisional application No. 61/597,202, filed on Feb. 10, 2012, provisional application No. 61/714,339, filed on Oct. 16, 2012.

(51) Int. Cl.
*A61F 5/01* (2006.01)

(52) U.S. Cl.
CPC ............ *A61F 5/013* (2013.01); *A61F 5/0118* (2013.01)

(58) Field of Classification Search
CPC combination set(s) only.
See application file for complete search history.

(56) References Cited

U.S. PATENT DOCUMENTS

| 2,361,506 A | 10/1944 | Smith |
| 2,961,785 A | 11/1960 | Toepfer |
| 3,369,258 A | 2/1968 | Smith |
| 4,013,070 A | 3/1977 | Harroff |
| 4,441,490 A | 4/1984 | Nirschl |
| 4,477,950 A | 10/1984 | Cisek et al. |
| 4,556,215 A | 12/1985 | Tarbox et al. |
| 4,575,075 A | 3/1986 | Tarbox et al. |

(Continued)

FOREIGN PATENT DOCUMENTS

| CN | 2528415 Y | 1/2003 |
| CN | 2635054 Y | 8/2004 |

(Continued)

OTHER PUBLICATIONS

International Search Report from corresponding PCT Application No. PCT/US203/025502 dated May 3, 2013.

(Continued)

*Primary Examiner* — Ophelia A Hawthorne
(74) *Attorney, Agent, or Firm* — Workman Nydegger

(57) ABSTRACT

A universal wrist brace is arranged for both right and left handed use. The wrist brace has a main body panel defining symmetrical first and second sides. Each of the first and second sides has a wing located at a distal end flaring outwardly from longitudinal side portions of the main body panel in a transverse direction of the main body panel and parallel to an upper edge portion. The main body panel defines an opening located between the first and second sides, proximate and adjacent to the upper edge portion. A main securing device is anchored to the first side of the main body panel and detachably attaches to the second side of the main body panel.

20 Claims, 9 Drawing Sheets

(56) References Cited

U.S. PATENT DOCUMENTS

| | | | |
|---|---|---|---|
| 4,617,017 A | 10/1986 | Hubbard et al. | |
| 4,854,309 A * | 8/1989 | Elsey | A61F 5/0118 602/21 |
| 4,862,563 A | 9/1989 | Flynn | |
| 4,883,073 A | 11/1989 | Aziz | |
| 4,953,568 A | 9/1990 | Theisler | |
| 4,960,114 A | 10/1990 | Dale | |
| 5,036,838 A | 8/1991 | Sherman | |
| 5,081,748 A | 1/1992 | Eberle | |
| 5,105,520 A | 4/1992 | Eberle | |
| 5,142,743 A | 9/1992 | Hahn | |
| 5,177,986 A | 1/1993 | Jensen | |
| D339,866 S | 9/1993 | Rice | |
| 5,267,943 A | 12/1993 | Dancyger | |
| 5,289,619 A | 3/1994 | Pileggi | |
| 5,300,037 A | 4/1994 | Delk et al. | |
| 5,307,521 A | 5/1994 | Davis | |
| D347,693 S | 6/1994 | Dancyger | |
| 5,335,916 A | 8/1994 | Nee | |
| D352,134 S | 11/1994 | Crowder | |
| D357,745 S | 4/1995 | Radwell | |
| 5,415,624 A * | 5/1995 | Williams | A61F 5/0104 602/14 |
| 5,511,756 A | 4/1996 | Spradling | |
| 5,513,657 A | 5/1996 | Nelson | |
| 5,548,871 A | 8/1996 | Trethewey | |
| 5,566,389 A * | 10/1996 | Li | A41D 13/088 2/16 |
| 5,600,849 A | 2/1997 | Hu | |
| 5,662,599 A | 9/1997 | Reich et al. | |
| 5,666,389 A | 9/1997 | Andersson et al. | |
| 5,722,092 A | 3/1998 | Borzecki et al. | |
| 5,728,059 A * | 3/1998 | Wiesemann | A61F 5/0118 128/878 |
| 5,733,249 A | 3/1998 | Katzin et al. | |
| 5,759,166 A * | 6/1998 | Nelson | A61F 5/0118 602/21 |
| 5,813,050 A | 9/1998 | Popowski | |
| 5,819,313 A | 10/1998 | McCrane | |
| D403,425 S | 12/1998 | Taylor et al. | |
| D405,180 S | 2/1999 | Reina | |
| 5,873,130 A | 2/1999 | Lafferty | |
| 5,928,172 A | 7/1999 | Gaylord | |
| 6,024,715 A | 2/2000 | Maxwell | |
| 6,029,321 A | 2/2000 | Fisher | |
| 6,049,953 A | 4/2000 | McCay et al. | |
| 6,059,694 A | 5/2000 | Villepigue | |
| 6,186,969 B1 | 2/2001 | Bell et al. | |
| 6,196,985 B1 | 3/2001 | Slautterback | |
| 6,261,252 B1 | 7/2001 | Darcey | |
| 6,308,387 B1 | 10/2001 | Borzi | |
| D456,081 S | 4/2002 | Bell et al. | |
| 6,385,821 B1 | 5/2002 | Modgil et al. | |
| 6,419,668 B2 | 7/2002 | Minato | |
| D461,901 S | 8/2002 | Rodgers | |
| 6,430,784 B1 | 8/2002 | Dudek et al. | |
| 6,449,815 B1 | 9/2002 | Spiller | |
| D465,068 S | 10/2002 | Payne | |
| 6,485,448 B2 | 11/2002 | Lamping et al. | |
| 6,517,501 B1 | 2/2003 | Slautterback | |
| 6,544,245 B2 | 4/2003 | Neeb et al. | |
| 6,561,994 B1 | 5/2003 | Mills et al. | |
| D477,088 S | 7/2003 | Brown et al. | |
| D477,409 S | 7/2003 | Mills et al. | |
| 6,622,346 B2 | 9/2003 | Graham et al. | |
| 6,662,374 B2 | 12/2003 | Leumi | |
| 6,681,454 B2 | 1/2004 | Modgil et al. | |
| 6,730,053 B1 | 5/2004 | Bodenschatz et al. | |
| 6,763,554 B1 | 7/2004 | Torrey et al. | |
| 6,775,896 B2 | 8/2004 | Dudek et al. | |
| 6,782,654 B1 | 8/2004 | Borchardt | |
| D496,465 S | 9/2004 | Weaver, II | |
| 6,785,909 B1 | 9/2004 | Li | |
| 6,826,807 B2 | 12/2004 | Inoue et al. | |
| 6,851,161 B2 | 2/2005 | Kingsford et al. | |
| 6,893,410 B1 * | 5/2005 | Hely | A61F 13/108 602/21 |
| 6,929,615 B2 | 8/2005 | Derr | |
| 6,960,176 B1 | 11/2005 | Hely et al. | |
| 7,033,331 B1 | 4/2006 | Hely | |
| 7,037,285 B2 | 5/2006 | Yewer, Jr. | |
| 7,056,298 B1 | 6/2006 | Weber | |
| 7,096,544 B2 | 8/2006 | Lusardi | |
| 7,132,144 B2 | 11/2006 | Roberts | |
| D533,280 S | 12/2006 | Wyatt et al. | |
| 7,219,405 B1 | 5/2007 | Nevens | |
| 7,318,812 B2 * | 1/2008 | Taylor | A61F 5/0118 602/21 |
| 7,334,354 B2 | 2/2008 | Foxen et al. | |
| 7,356,888 B2 | 4/2008 | Chao et al. | |
| 7,361,154 B2 | 4/2008 | Jablonka et al. | |
| 7,402,148 B2 | 7/2008 | Brewer | |
| 7,402,149 B1 | 7/2008 | Garelick et al. | |
| 7,442,177 B1 | 10/2008 | Garelick et al. | |
| 7,452,343 B2 | 11/2008 | Campbell | |
| 7,455,650 B1 | 11/2008 | Garelick et al. | |
| 7,473,236 B1 | 1/2009 | Mathewson | |
| 7,537,577 B2 * | 5/2009 | Phelan et al. | 602/21 |
| 7,587,796 B1 | 9/2009 | Schultz | |
| 7,588,216 B1 | 9/2009 | Hoyl et al. | |
| 7,624,480 B2 | 12/2009 | Coronel | |
| 7,636,987 B2 | 12/2009 | Derscheid et al. | |
| 7,645,250 B2 | 1/2010 | Koby et al. | |
| 7,708,709 B2 | 5/2010 | Brewer | |
| 7,712,155 B1 | 5/2010 | Pantoja | |
| 7,713,223 B2 | 5/2010 | Weber et al. | |
| 7,713,224 B1 | 5/2010 | Peters et al. | |
| 7,793,892 B1 | 9/2010 | Bowen et al. | |
| D626,242 S | 10/2010 | Sagnip et al. | |
| 7,874,997 B2 * | 1/2011 | Jaccard | A61F 5/0118 128/846 |
| 7,914,475 B2 | 3/2011 | Wyatt et al. | |
| 7,921,525 B1 | 4/2011 | Lucas | |
| 7,979,088 B2 | 7/2011 | Diciolla | |
| 8,016,492 B2 | 9/2011 | Pyle | |
| 8,069,540 B2 | 12/2011 | Obiols et al. | |
| 8,070,699 B2 | 12/2011 | Avitable et al. | |
| 8,647,288 B2 * | 2/2014 | Jorissen | A61F 5/0118 602/20 |
| 2002/0082538 A1 | 6/2002 | Holland et al. | |
| 2003/0110596 A1 | 6/2003 | Graham et al. | |
| 2004/0049141 A1 | 3/2004 | Slautterback et al. | |
| 2005/0197608 A1 | 9/2005 | Taylor et al. | |
| 2005/0197609 A1 | 9/2005 | Mills | |
| 2005/0273030 A1 | 12/2005 | Koby et al. | |
| 2006/0032032 A1 | 2/2006 | Cheng | |
| 2006/0287626 A1 * | 12/2006 | Bennett | A61F 5/0118 602/22 |
| 2007/0129658 A1 | 6/2007 | Hampson et al. | |
| 2007/0225630 A1 | 9/2007 | Wyatt et al. | |
| 2008/0066272 A1 | 3/2008 | Hammerslag et al. | |
| 2008/0287848 A1 | 11/2008 | Jaccard | |
| 2009/0012438 A1 | 1/2009 | Frangi | |

FOREIGN PATENT DOCUMENTS

| | | |
|---|---|---|
| CN | 2824882 Y | 10/2006 |
| DE | 19525671 A1 | 1/1997 |
| WO | 2007051524 A2 | 5/2007 |

OTHER PUBLICATIONS

"Basic Hand Anatomy", American Society for Surgery of the Hand, at least prior to Mar. 21, 2007, 6 pages.

International Search Report from PCT/US2007/07076, dated Dec. 26, 2007, 1 pages.

European Search Report from European application No. 07753684.5, dated Aug. 5, 2010, 6 pages.

(56) References Cited

OTHER PUBLICATIONS

European Office Action from Application No. 13 706 834.2, dated Nov. 17, 2016.

* cited by examiner

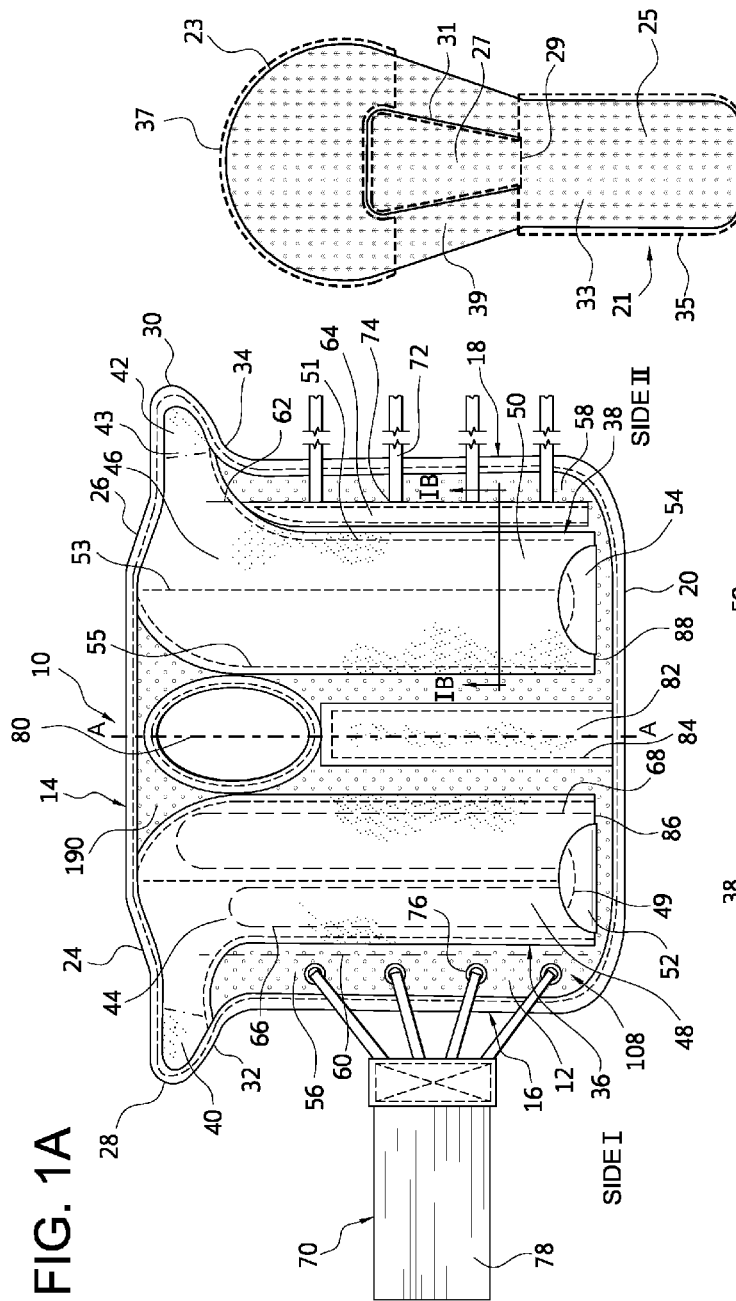

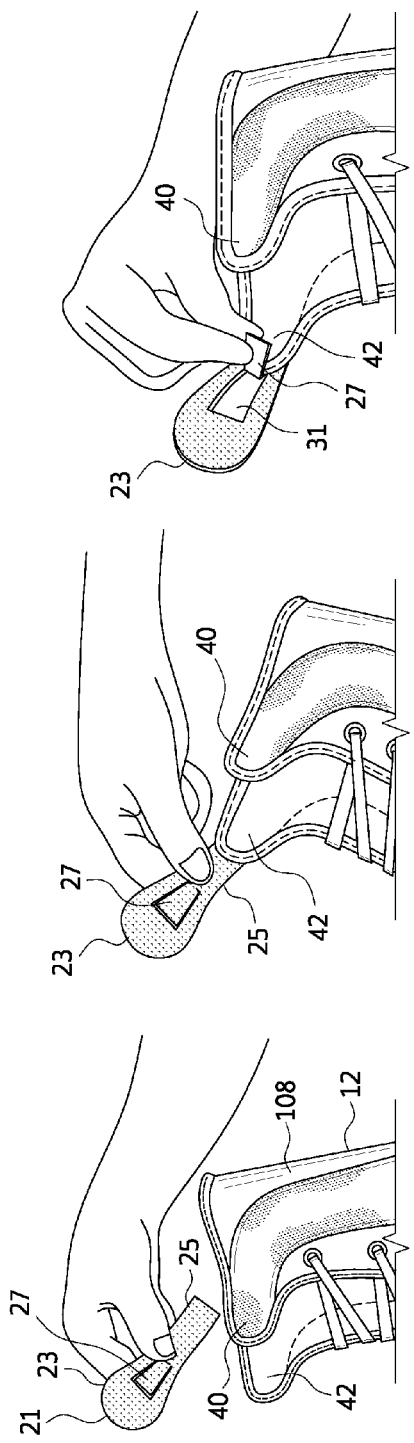
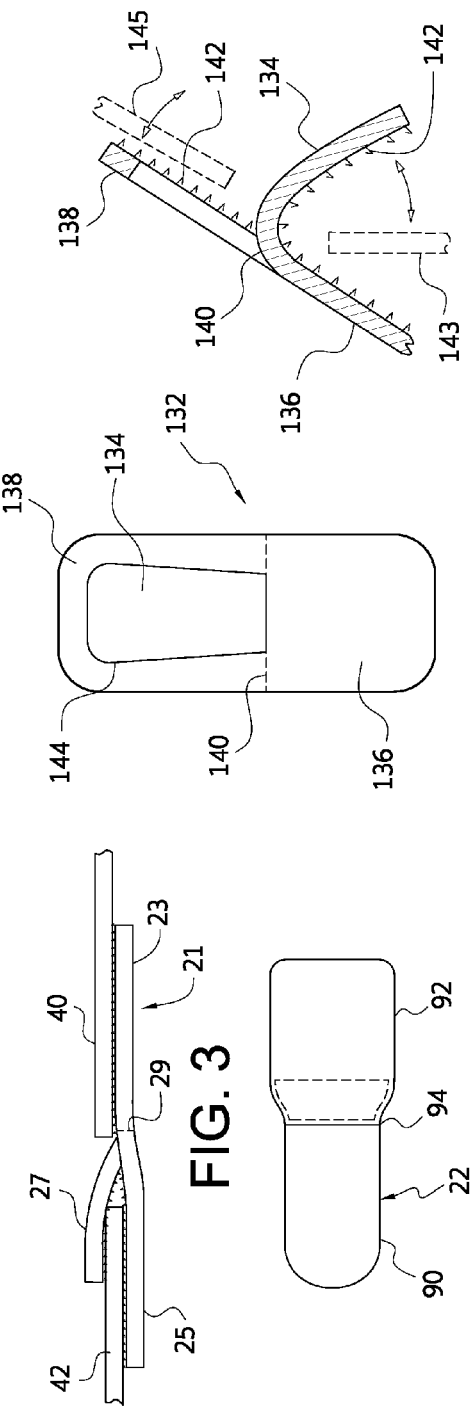
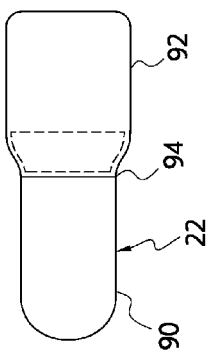

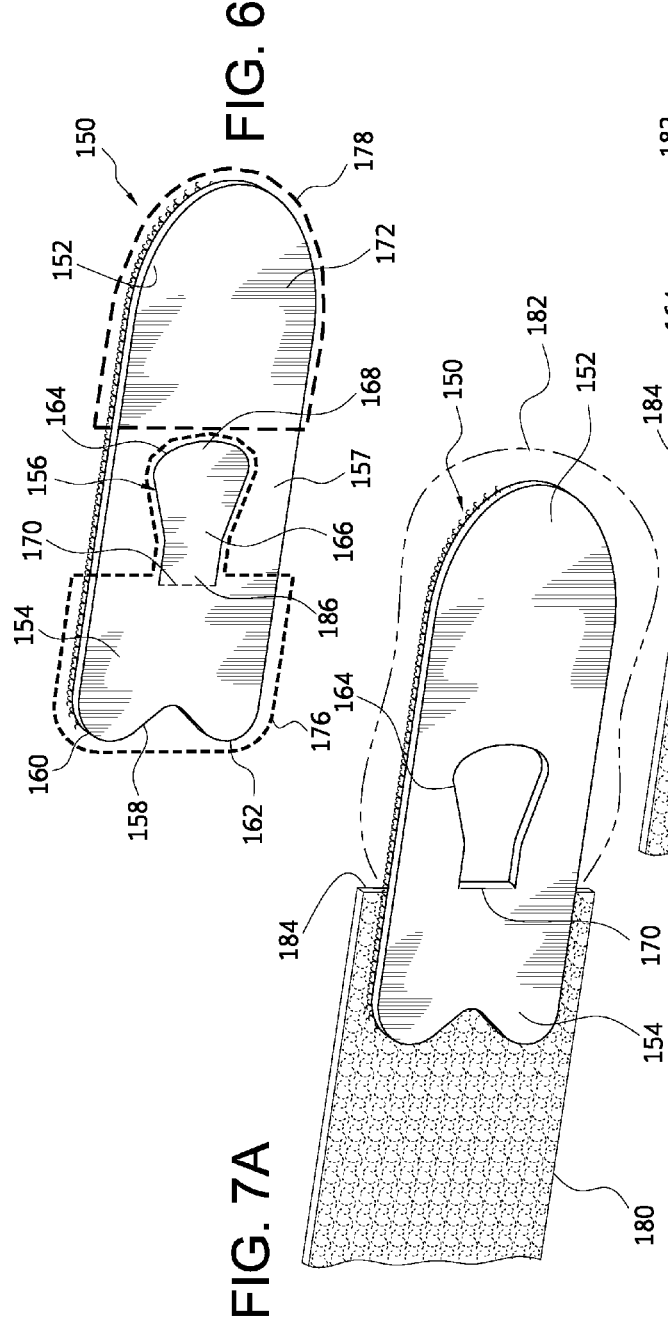

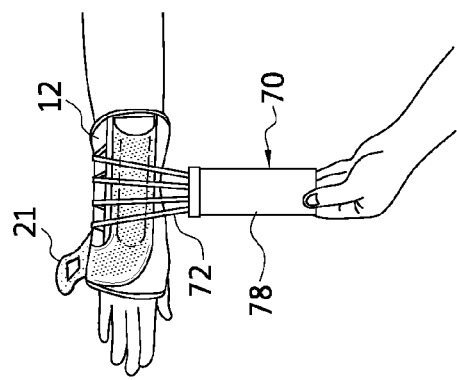
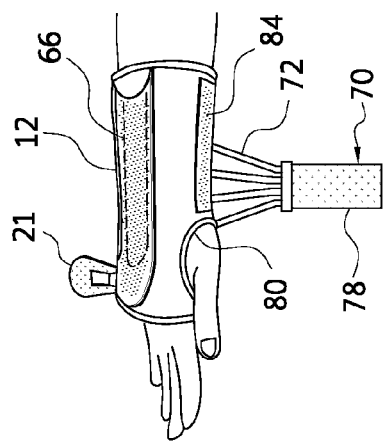
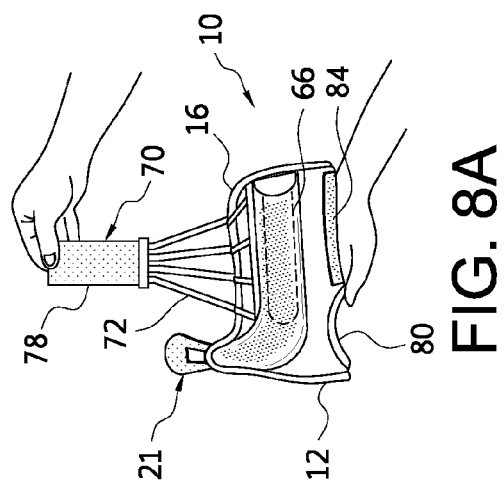
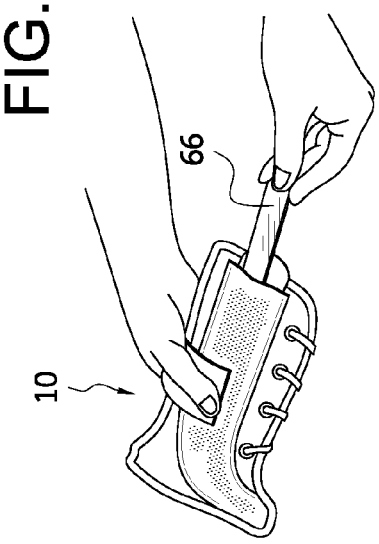
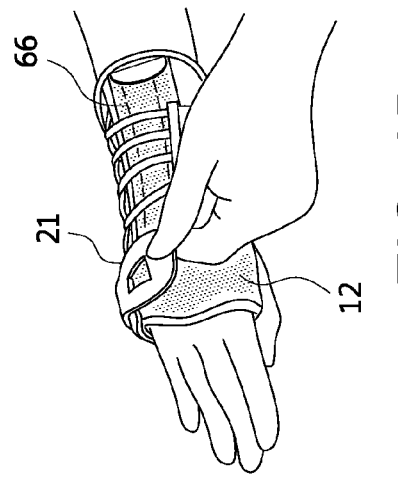

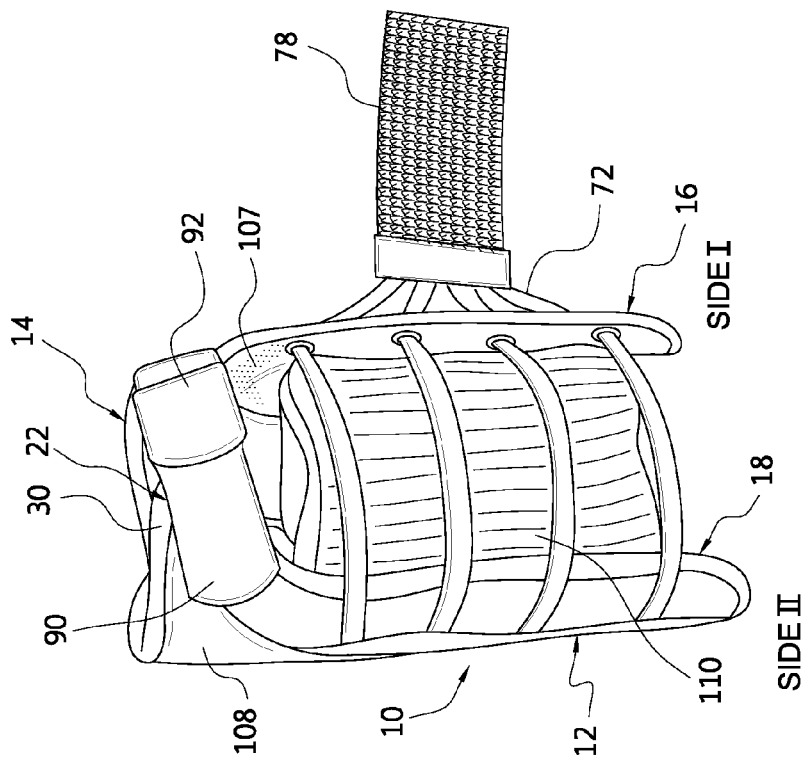
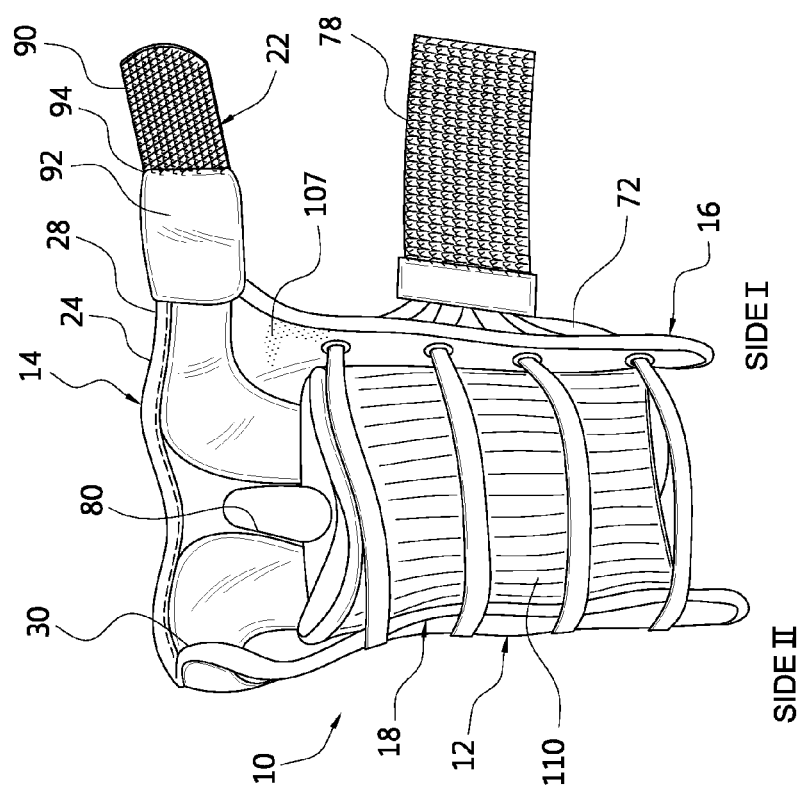
FIG. 9A
FIG. 9B

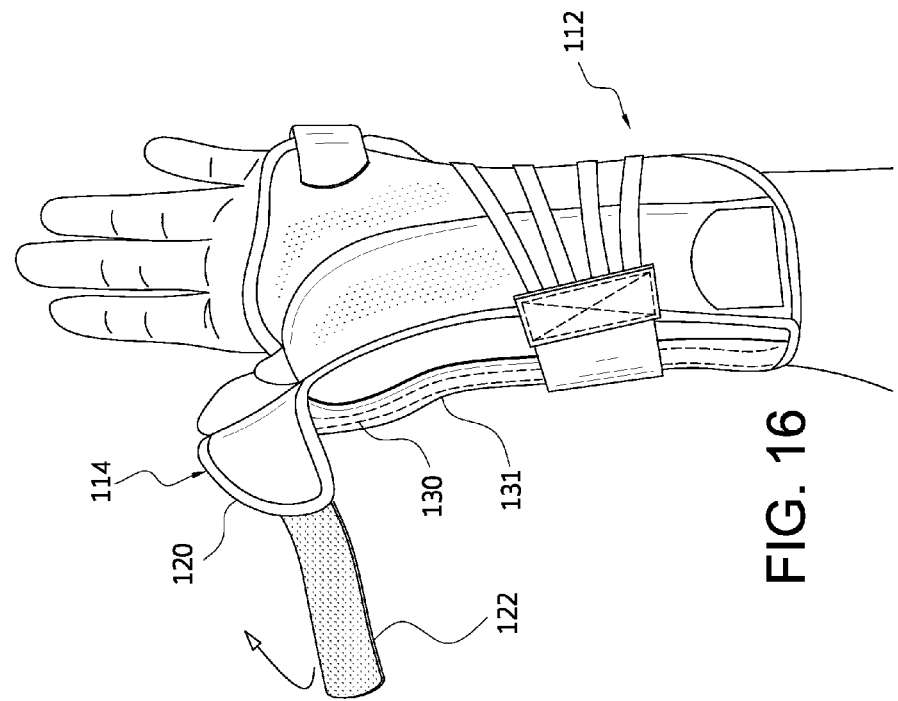
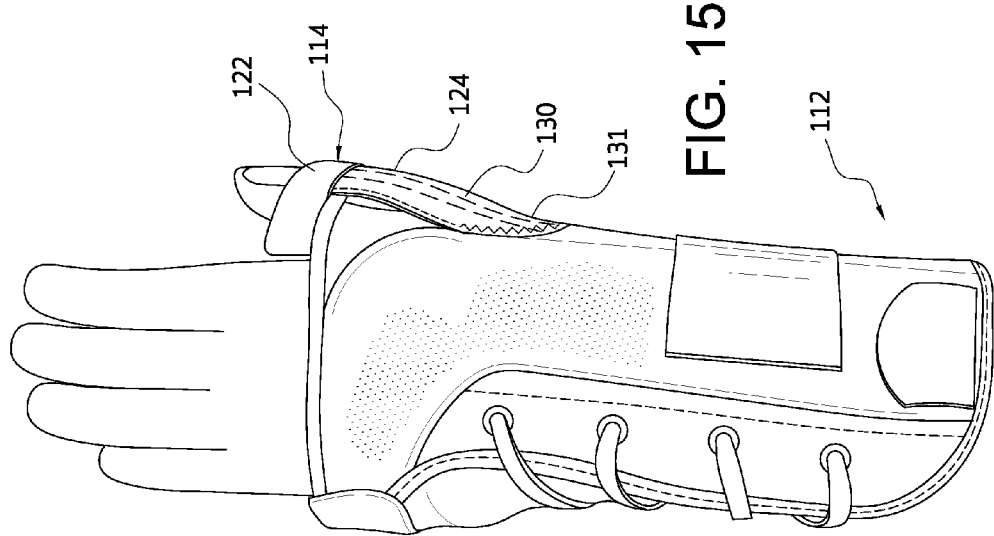

WRIST BRACE AND METHOD AND COMPONENTS FOR SECURING THE SAME

FIELD OF ART

The disclosure relates to orthopedic devices, and more specifically to wrist braces, and methods and components used for securing the same. The wrist brace is universal and adaptable for either left or right sided use for rehabilitation and injury prevention.

BACKGROUND

Numerous orthopedic supports and braces are available to provide therapeutic support or immobilization of a limb or extremity of a patient. Such supports and braces range from simple elastic or soft good bandages and braces to complicated mechanical devices. Hand and wrist braces including means for supporting a thumb or other digit often comprise an elastic or soft good member that may be wrapped about the patient's hand, wrist, or other digit. These braces may be supplemented for one or more particular therapeutic purposes by adding rigid or semi-rigid support members, stays, splints, or the like.

It is desired for an orthopedic brace to apply to a limb or extremity in a position or orientation to achieve a good fit. A wrist brace that includes a palmar stay intended to support the hand in a "cock-up" position, must be positioned so the palmar stay is located along the palmar side of the wrist and hand, and a bend in the distal portion of the palmar stay is angled toward, rather than away from, the palm of the hand. Similarly, a wrist brace that includes dorsal supports is arranged to position the dorsal supports along the dorsal side of the wrist.

Even a brace that includes no support members, such as the aforementioned palmar and dorsal stays, may be shaped according to particular features of a limb. A wrist brace often extends well onto the hand, and may have a distal portion contoured or configured to be wrapped about the hand between the thumb and forefinger.

Given the need to apply an orthopedic brace in a position or orientation relative to a part of a limb, known orthopedic braces are typically configured for only left or right sided use. Unfortunately, many known left and right sided braces are not interchangeable; that is, a left handed wrist brace cannot be used on a right wrist, and vice versa.

This can be more fully appreciated by recalling the example previously described wherein a wrist brace includes a palmar stay intended to support the hand in a "cock-up" position. In this example, to simply apply a left handed brace to the right wrist "backwards," by turning the left handed brace "inside out," does not reverse the palmar stay and would be ineffective because the palmar stay is not reoriented into the correct position for the right hand.

Further, and more generally, straps or fasteners located on the outside of a left handed brace, when applied to the left hand, would be located on the inside of the left handed brace when "turned inside out" for right handed use, therefore becoming useless or causing discomfort for a wearer of the brace. Thus, it is necessary for physicians, physical therapists, medical suppliers, and the like, to maintain a supply of both left and right handed braces.

Many known braces restrict the locations at which straps are secured to a main body soft-good pad. These braces employ patches of corresponding hook and loop material on the straps and the main body, respectively. By restricting the locations of hook and loop material, a wearer is limited at where the strap will secure on the main body. Known braces also lack flexibility to accommodate different straps and extensions from the main body that allow for securing a variety of appendages.

Besides the drawback of known braces typically being restricted for either left or right handed use, many known braces are limited as to their ability to accommodate certain sizes of appendages. As is well understood, injured wrists, hands or digits (i.e., thumb and fingers), often swell as they heal. A brace used to support these appendages must be adaptable to various sizes of injured wrists, hands or digits as they undergo healing. In view of these size variations of the wrists, hands or digits, and the possibility of dressings being used in combination with the brace, it is desirable to provide a brace that enables a wide range of size adjustability.

SUMMARY

Certain orthopedic device embodiments described herein and the features thereof result in a single wrist brace that may be used for both left and right sided applications, otherwise known as "universal," eliminating the need for physicians, physical therapists, medical suppliers, and others, to maintain a supply of both left and right sided braces. The embodiments also enable a single brace to accommodate a wide variety of hands, wrist and digits, reducing the sizes that are necessary for storage, and enabling the wearer to adjust the brace according to degrees of swelling or to allow for greater comfort. The universality of the wrist brace embodiments permit them to be suitable for both left and right sided application, and can be compactly packaged and stored.

The universal wrist brace is configured to treat a broad range of indications including carpal tunnel syndrome, arthritis, strains and sprains, post-cast healing and other selected wrist injuries. Variations of the wrist brace are adapted to a universal thumb brace arranged to treat indications such as Gamekeeper's thumb, DeQuervain's tendonitis, selected scaphold injuries, and other soft tissue injuries.

In a first embodiment, the wrist brace is adapted for both right and left handed use. The wrist brace has a main body panel defining generally symmetrical first and second sides. The main body panel defines a first side portion generally extending in a longitudinal direction relative to and along the first side of the main body panel, an upper edge portion generally extending in a transverse direction relative to and along the main body panel, and a first wing flaring and extending away from the first side portion in the generally transverse direction, and located between the upper edge portion and the first side portion along the main body panel. A fastening strap is secured to the second side of the main body panel, and connects to the first wing. The main body is preferably formed from a soft good, such as a breathable felt material, to provide increased comfort and compliance to the hand.

The main body panel may include a second side portion generally extending in a longitudinal direction along the second side of the main body panel, and a second wing flaring to extend away from the second side portion in the generally transverse direction, and located between the upper edge portion and the second side portion. Contoured upper edge sections may extend obliquely in the transverse direction from the upper edge portion to the first and second wings.

The configuration of the wrist brace, particularly in view of the upper edge portion and the wings, provides a lateral hand stabilizer allowing for a more custom fit and further enhances ulnar deviation control.

The main body may include a first securing pad generally following a trajectory of the first wing and the upper edge portion in the transverse direction and following a trajectory of the first side portion in the longitudinal direction. A second securing pad may be similarly provided on the second side of the main body panel.

The main body panel may define a thumb opening generally located between the first and second sides, proximate and adjacent to the upper edge portion. The opening may have a generally oval and elongate shape extending along the longitudinal direction. The configuration of the thumb opening allows for a variety of thumb shapes and can accommodate the thumbs of both right and left hands.

The wrist brace can include a thumb attachment secured to the main body panel about only a lower portion of the thumb opening. The thumb attachment may be stitched to the main body panel about a lower portion of the thumb opening, or may be removably attached to the main body panel. The thumb attachment protrudes outwardly from the main body panel and projects toward and preferably beyond the upper edge portion of the main body portion. The thumb attachment includes first and second flaps movable relative to the main body panel, and has a secure tab adapted to transform the thumb attachment from a generally flat configuration into a circumferential configuration.

A thumb stay preferably extends along the longitudinal length of the main body panel, and extends in the main body panel between the first and second sides up to the opening. From the opening, the thumb stay includes an outward bend and extends from such bend along the length and within the thumb attachment.

The wrist brace may have a main securing device including a plurality of laces anchored to the second side of the main body panel. The laces pass through a plurality of eyelets located on the first side of the main body panel. The main securing device further includes a tab carrying the laces and adapted to secure over the main body panel. The main securing device provides for a single pull closure system allowing for quick and easy adjustment of the wrist brace.

The main body panel may define at least one pocket located along one of the first and second sides. The pocket defines first and second subpocket regions, whereby the first subpocket region extends directly below at least a portion of the second subpocket region. A first stay is arranged to be received by the first subpocket region, and a second stay is arranged to be received by the second subpocket region. The second stay may have a different width from a width of the first stay. The pocket is preferably elongate and extends in the longitudinal direction of the main body panel, and includes closure flaps for removing and adjusting the stays.

Each of the subpocket regions may include yet further pockets located therein. The first subpocket may form two pockets that are sized substantially the same and arranged to receive dorsal stays that can be located adjacent to each other when in the two pockets. The second subpocket may define a pocket adapted to receive a palmar stay that is substantially wider than a dorsal stay, and another pocket by be located alongside the palmar say pocket, and adapted to receive an additional stay, such as a stay shaped like the dorsal stays.

A securing device having a first end with a pair of flaps clamps onto the second side of the main body, and a second end carries a locking tab that secures to the first side of the main body panel.

According to an embodiment, the securing device is arranged to removably secure to each of the sides of the main body panel to join the two sides together. The securing device is preferably a unitary strip having a plurality of hook elements located along a first surface. The securing device has first and second portions secured to the first and second opposed sides, respectively. The first portion defines an elongate first anchor tab and a second anchor tab extending from the fold line and adapted to bend toward the first anchor tab to form a clasp therewith. The second portion defines a tab head extending beyond the first anchor tab. The first and second anchor tabs are clamped onto the first and second surfaces, respectively, on the first side of the main body panel, and the tab head secures to the first surface of the second side of the main body panel.

The first and second portions of the securing device have substantially the same surface area to provide generally equal traction on both sides of the main body panel. The tab head may have a bulbous or bullet-like shape. The first anchor tab is generally elongate, and may define and end portion defining a notch to differentiate from the tab head, and make it more difficult to remove the first anchor tab from the main body panel.

The second anchor tab has a bend area adapted to secure to and bend over an edge portion defined by the main body panel. The second anchor tab may define an anchor neck extending beyond the bend area, and also define an anchor head extending from the anchor neck and having a greater width than the anchor neck to firmly grasp the surface of the main body panel.

The second anchor tab may be bordered outside of a fold line by an opening formed by the unitary strip. The securing device may include side areas extending along sides of the opening and adapted to supplement traction of the tab head.

The securing device is flexible, and has a second surface devoid of hook elements. While described to secure two sides of the main body panel, the securing device may secure a variety of two bodies having hook receivable surfaces, including straps, patches, and other known articles having hook receivable surfaces. The tab head is not limited to having hook receivable elements, but may carry other fasteners such as snaps, hooks, flanges, or other known elements for coupling two components to one another.

The numerous advantages, features and functions of the embodiments of the wrist brace and the methods for using the same, and components for use therewith, such as the securing device, will become readily apparent and better understood in view of the following description and accompanying drawings. The following description is not intended to limit the scope of the wrist brace, but instead merely provides exemplary embodiments for ease of understanding.

BRIEF DESCRIPTION OF THE DRAWINGS

FIG. 1A is a top plan view of a first wrist brace embodiment according to the disclosure.

FIG. 1B is a schematic cross-sectional view taken along line IB-IB in FIG. 1A.

FIG. 1C is a plan view of a securing device embodiment for use with the wrist brace of FIG. 1A.

FIGS. 2A-2C show how to attach the securing device of FIG. 1C onto the wrist brace of FIG. 1A.

FIG. 3 is a schematic view of the securing device of FIG. 1C on the wrist brace of FIG. 1A.

FIG. 4A is a plan view of another securing device embodiment in a flat, closed configuration.

FIG. 4B is a side view of the securing device of FIG. 4A in a bent, open configuration.

FIG. 5 is a plan view of another securing device embodiment.

FIG. 6 is a perspective view of another securing device embodiment.

FIGS. 7A-7B are schematic perspective views showing front and rear views of the securing device of FIG. 6 attached onto first and second bodies.

FIGS. 8A-8E exemplify how to attach the first wrist brace embodiment on a wrist.

FIG. 9A is a perspective view of the wrist brace of FIG. 1A, showing the wrist brace in an open configuration.

FIG. 9B is a perspective view of the wrist brace of FIG. 1A, showing the adjustable fastening strap in a closed configuration.

FIG. 15 is a perspective view of the wrist brace of FIG. 13 showing the thumb attachment in a closed configuration.

FIG. 16 is a perspective view of the wrist brace of FIG. 13 showing the thumb attachment in an open configuration.

Figure 12:
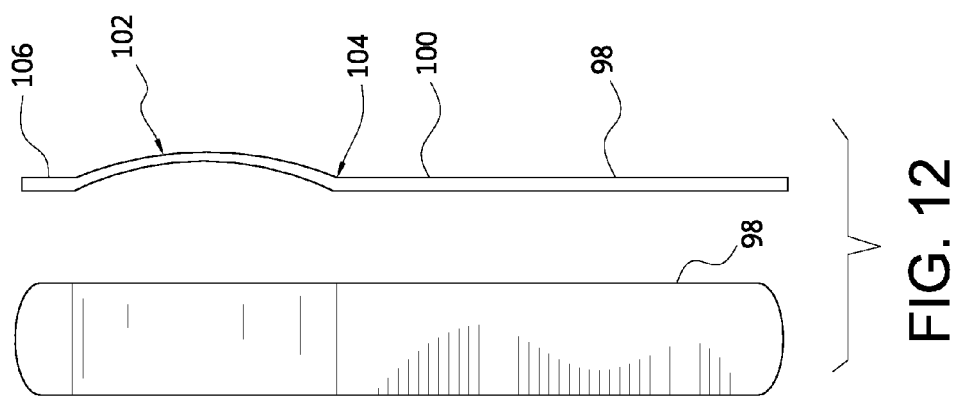
FIG. 12 includes a top plan view and a side view of a palmar stay for the wrist brace of FIG. 1A.

In the various figures, similar elements are provided with similar reference numbers. The drawing figures are not necessarily drawn to scale, or proportion, but instead are drawn to provide a better understanding of the components, and are not intended to be limiting in scope, but rather provide exemplary illustrations.

DETAILED DESCRIPTION OF VARIOUS EMBODIMENTS

For further ease of understanding the exemplary embodiments of an orthopedic device in the form of a wrist brace as disclosed, a description of a few terms is necessary. As used, the term "dorsal" has its ordinary meaning and refers to the top surfaces of the hand, foot, ankle and foreleg or shin. As used, the term "palmar" has its ordinary meaning and refers to a palm of a hand. As used, the term "proximal" has its ordinary meaning and refers to a location where the appendage joins the body. Likewise, the term "distal" has its ordinary meaning and refers to a location used for the point furthest from the point of attachment to the body. The term "inner" also has its ordinary meaning and refers to a side or location adjacent to a hand. The term "outer" has its ordinary meaning and refers to a location opposite an inner surface, and is the side or surface situated on the outside of the wrist brace.

The terms "rigid," "flexible," and "resilient" may be used to distinguish characteristics of portions of certain features of the wrist brace. The term "rigid" should denote that an element of the device is devoid of flexibility. Within the context of support members or shells that are "rigid," it is intended to indicate that they do not lose their overall shape when force is applied, and in fact they may break if bent with sufficient force. The term "flexible" should denote that features are capable of repeated bending such that the features may be bent into retained shapes or the features do not retain a general shape, but continuously deform when force is applied. The term "resilient" is used to qualify such flexible features as returning to an initial general shape without permanent deformation. As for the term "semi-rigid," this term is used to connote properties that may have some degree of flexibility or resiliency.

In referring to a first wrist brace embodiment depicted in FIG. 1A wherein the brace 10 is shown in a substantially flat configuration. The brace 10 includes a main body panel 12, having an upper or distal transverse edge 14, first and second opposed side edges 16, 18 generally longitudinally arranged relative to the upper edge 14, and a lower or proximal edge 20 opposed to the upper edge 14 that is likewise transverse. The main body panel 12 is preferably constructed from a breathable soft good, such as a breathable felt material, and defines portions that are hook receivable.

A soft good may be a woven, warp knit, circular knit, nonwoven or lamination assembly. The main body panel may be a laminated assembly including a flocked velvet material on a woven scrim (for support). The main body panel may also include a polyurethane film laminated to a non-woven felted backing. Various openings 190 may be formed through the soft good. The non-woven felted backing, among other materials, is preferably a hook receivable material that enables conventional hook elements to securely engage therewith.

First and second distal wings 28, 30 are defined at the upper or distal corner of each first and second side edges 16, 18. The wings 28, 30 flare outwardly from the generally longitudinal side edges to form a widened distal end of the main body panel 12. First and second upper contoured edge portions 24, 26 extend from the upper edge 14 to the wings 28, 30, and first and second side contoured edge portions 32, 34 transition from the side edges 16, 18. This configuration provides enhanced support for the mid-section of a hand which anatomically widens from the wrist, and the configuration of the wings gradually flares outwardly to accommodate this mid-section of the hand. As illustrated in FIG. 1C, an adjustable auxiliary securing device 21 is provided for securing to the opposed first and second side edges 16, 18 at the first and second wings 28, 30 to close the wrist brace at the distal end.

As shown from FIG. 1A, the contours of the first and second sides I, II of the main body panel are generally symmetrical along a central, longitudinal axis A-A dividing the first and second sides from one another. The symmetry allows for the wrist brace to be worn on either the left or right hands, and therefore contributes to the universality of the wrist brace.

First and second securing pads 36, 38 are located on the main body panel 12, and generally follow the contours. The securing pads 36, 38 include respective wing sections 40, 42 extending into and following the trajectory of the wings in a transverse manner, longitudinal support sections 48, 50 extending along the length of the main body panel, and transitory sections 44, 46 that bend from the wing sections 40, 42 to the support sections 48, 50.

Each of the securing pads 36, 38 define pockets 52, 54 with the main body panel 12 arranged to secure various uniquely configured and dimensioned dorsal and palmar stays 66, 68, according to right or left hand configurations, within openings 86, 88 formed between the main body panel 12 and the securing pads 36, 38. Alternatively, the pockets 52, 54 may have the same shape to interchangeably receive various stays.

Closure flaps 49 are on the brace to close the openings 86, 88, and retain the stays within the pockets. The pockets may define a plurality of inner pockets that can accommodate both dorsal and palmar stays and combinations.

FIG. 1B depicts an arrangement of various pockets that can receive both palmar and dorsal stays. The arrangement of various pockets may be the same on both sides of the brace to be useable in both right and left hand wrist brace configurations. The wrist brace includes upper pockets defining a palmar stay pocket 57, and a dorsal stay pocket 59, and a lower series of first and second dorsal stay pockets 61, 63 underneath the upper pockets. The palmar stay pocket 57 is specifically sized to securely retain the palmar stay, whereas the dorsal stay pocket 59 is arranged to securely retain the palmar stay. A dorsal stay can be retained within the palmar stay pocket 57, and the dorsal stay may be configured to be securely retained within the dorsal stay pocket 59. The lower series of dorsal stay pockets 61, 63 are solely configured and dimensioned to securely receive dorsal stays.

In the arrangement, the securing pad 38 delimits the upper surface of upper pockets 57, 59 whereas an upper surface 108 of the main body panel forms part of the lower surface of only the palmar stay pocket 57, and another part of the lower surface of the palmar stay pocket 57 is defined by an inner layer 109. The lower surface of the upper dorsal stay pocket 59 is only defined by the inner layer 109. The upper surface of the lower series of dorsal stay pockets 61, 63 is defined by the inner layer 109, and the lower surface of the lower series of dorsal stay pockets 61, 63 is defined by the upper surface 108 of the main body panel.

Inner and outer stitching lines 51, 55 delimit a first boundary of the palmar stay pocket 57 and a first boundary of the dorsal stay pocket 59, and a middle stitching line 55 divides the palmar and dorsal stay pockets 57, 59. Inside inner stitching line 65 is spaced away from the inner stitching line 51 and defines a first boundary of the first lower dorsal stay pocket 61, and the middle stitching line 53 defines a first boundary of the second lower dorsal stay pocket 63. The middle stitching line 53 divides both the lower series of dorsal stay pockets 61, 63. As shown, the lower series of dorsal stay pockets 61, 63 may be equally sized.

From the upper and lower series of pockets, various combinations of stays may be used according to the indications for the wearer, and the configuration of the wrist brace. A palmar stay is securely in the palmar stay pocket along the first side, and first and second dorsal stays may be in both the first and second lower series of dorsal stay pockets.

The main body panel 12 defines a thumb hole 80 centrally located between the first and second sides I, II and formed at the upper or distal end of the wrist brace. The thumb hole is shown as having a substantially elongate and oval form, however its shape is not limited to that shown, but can assume a variety of shapes that can accommodate a thumb being inserted therethrough. A thumb pad 82 is located along the mid-section of the main body panel 12, and extends adjacent to the thumb hole 80 to the lower edge 20. The thumb pad 82 may be constructed similarly to the securing pads 36, 38, and a thumb stay 84 may be permanently or removably placed between the main body panel and the thumb pad 82.

In returning to FIG. 1A, the securing pads 36, 38 preferably have surfaces that are arranged for receiving hook material, such as unbroken loop material. This allows for the auxiliary securing device to be mounted over a plurality of locations as considered suitable by the wearer. Also, a main securing device 70, as discussed more fully below, can be secured over a plurality of locations over the surface of the main body panel as well. An additional securing pad 64 may be provided along one of the securing pads 36, 38 to widen the area on the main body panel for fastening the main securing device thereto.

Areas 56, 58 of the main body panel are also free from the securing pads, and these pad-free areas are adjacent the first and second side edges 16, 18. The pad-free areas 56, 58 may include creases 60, 62 that facilitate donning of the brace allowing the brace to more closely conform to the wearer's wrist. Such creases may also be found in the securing pads as well, such as at the tips of the wings 40, 42.

In this embodiment, the main securing device 70 is a lace-type securing device which includes a plurality of laces 72 having second ends anchored to the second side II of the main body panel 12 at an anchoring point 74 adjacent the additional securing pad 64. The laces 72 extend across to the first side I of the main body panel 12 and feed through eyelets 76, and are redirected to the second side II of the main body panel 12. First ends of the laces are carried by a strap tab 78 adapted to be secured among the securing pads 36, 38. The wrist brace is not limited to lace type main securing devices, but may include any type of securing device suitable for bringing the first and second sides I, II together including strapping systems such as those discussed in U.S. Pat. No. 7,914,475 incorporated by reference, and dial tensioning and cable devices discussed in U.S. patent application publication 2008/0066272, incorporated by reference.

The main securing device allows for size adjustment and additional comfort. The main securing device may be divided into multiple series of a plurality of laces, and may possess multiple strap tabs 78 that correspond to each series of a plurality of laces, according to the length of the wrist brace. A longer wrist brace than the wrist brace depicted in FIG. 1A that extends along the forearm toward the elbow may include two main securing devices spaced along the wrist brace and forearm of the wearer.

In reference to FIG. 1C, the adjustable auxiliary securing device 21 is arranged to removably secure to each of the opposed sides, such as at the tips of the wings 40, 42 of the main body panel to join the two sides together. The securing device is preferably a unitary strip having a plurality of hook elements located along one surface 33 whereas that other surface opposite the hook elements may include a brushed loop or other non-engaging type surface. The securing device 21 has first and second portions 35, 37 divided by a fold line 29 extending transversely across a width of the securing device. The first portion 35 is defined as including an elongate first anchor tab 25 and a second anchor tab 27 extending from the line 29. The second portion 37 includes a tab head 23 extending from at least the line 29 and surrounds second anchor tab 27 beyond the line 29.

The tab head 23 is defined by the outer periphery of the second portion and is delimited along its inner periphery by the profile of the second anchor tab 27. An opening 31 has a profile generally corresponding to the second anchor tab 27 above the fold line, which permits the second anchor tab 27 to fold toward the first anchor tab 25.

It is preferable in this embodiment that the tab head 23 is rounded or at least has a greater width than the first anchor tab 25 to provide sufficient surface area in view of the second anchor tab 27 to firmly secure to the outer surface of the main body. By flaring the tab head 23 from the first portion, the tab head 23 shape can better conform to the shape of the contour of the wrist brace and leave less of the hook elements not secured to any surface exposed such as side portions 39 below the majority of the tab head and extending alongside the second anchor tab 27. The first and second portions 35, 37 preferably have substantially the same surface area for grasping opposed straps, surfaces or other bodies by which the securing device secure to one another.

As shown the second anchor tab 27 has a smaller surface area than the first anchor tab 25. While the first anchor tab 25 has a longer length, it has been found that the combination of the first and second anchor tabs 25, 27 sufficiently can grasp an object despite the first anchor tab 25 having a longer length and more surface area than the second anchor tab 27. The second anchor tab 27 is preferably shorter so it extends less into an inner surface of a brace, or strap so as not to cause discomfort to the wearer.

While described as having different lengths, other variations envision that the first and second anchors may have substantially the same surface area depending on the application. While it is preferred that the first portion including the anchor tabs has generally the same surface area as the second portion including the tab head to maintain substantially equal grasping of two opposed bodies, the embodiments are not limited to this configuration and may have different spatial and surface area relationships.

FIGS. 2A-2C show how the securing device 21 can be mounted on two sides of the wrist brace, particularly at the wing tips 40, 42. The first anchor tab 23 is fixedly secured to an outer hook receivable surface of the main body panel 12 such that the line 29 extends beyond the wing tip 42. The second anchor tab 27 is flexed at the line 29 over the wing tip 42 to secure to an inner hook receivable surface 107 of the main body panel. At this point, both the first and second anchor tabs 25, 27 clamp onto the wing tip 42, as shown in FIG. 3.

In this embodiment, it is preferable that the second anchor tab 27 extend minimally along the inner surface of the wrist brace so to have a minimal footprint and therefore not cause any discomfort to the wearer of the brace. A loop island 43 may be provided along the inner surface to enhance the grasping ability of the hook elements of the second anchor tab 27 along the inner surface of the wrist brace. Loop islands may be at other areas of the wrist brace to likewise improve the ability to secure various straps and components.

FIG. 4A shows a variation of the securing device 132 according to FIG. 1C, and having a surface with hook elements 142. In this variation, the first portion defines the first anchor tab 136 delimited from the second portion by line 140. The second portion defines a tab head 134 surrounded by a second anchor tab or frame 138. In this variation, as shown in FIG. 4B, the first and second anchor tabs 136, 138 are bendable relative to one another to form a clamp whereby both the first and second anchor tabs 136, 138 generally have the same length and are arranged to clamp opposed sides of a body 143 having hook receivable surfaces. The tab head 134 extends outwardly from the line 140 through an opening 144 to secure onto a surface of another body 145 having a hook receivable surface.

The securing device is preferably formed from a single strip of flexible material having a surface with hook elements. The second anchor or the tab head are preferably die cut from the single strip. The securing device provides both a structure and method that allows for simple and quick adaptation of a brace to include additional strap elements. When converting the wrist brace from a right hand brace configuration to a left hand brace configuration, the securing device can be removed in total, and secured to an opposite side according to the preferred configuration of the brace. The securing device is not limited to the configurations described, and other relationships and shapes may be provided according the specifications of the brace or other device requiring such securing device.

As shown in FIG. 5, another embodiment of the auxiliary securing device 22 includes a secure tab 90, a locking part 92 and a joint 94 located therebetween. Both the secure tab 90 and the locking part 92 are arranged to engage the securing pads 36, 38 to engage the first and second sides I, II of the main body panel. The locking part 92 is preferably defined as a pair of flaps which have opposed faces arranged to clamp onto one of the wing pad sections 40, 42 (both the inner and outer surfaces 107, 108 of the main body panel 12 may have hook receivable sections) whereas the secure tab 90 is arranged to secure to the other wing pad section 40, 42 on the outer surface of the main body panel.

FIGS. 6 and 7A-7B depict another embodiment of a securing device 150 arranged for securing two bodies 180, 182 to one another. The securing device 150 can secure first and second strap ends to one another. The securing device 150 has a width generally similar to the width of a strap, as shown in FIGS. 7A and 7B. The securing device 150 can secure to an edge portion 184 of a strap 180, and secure to the other body such as a panel or another strap. The securing device 150 is removable from the strap 180, and the strap 180 can be trimmed to accommodate the anatomy of a wearer, and the securing device 150 can be secured to the newly trimmed edge portion 184.

The securing device 150 preferably defines a surface 174 having a plurality of hook elements adapted to secure to both the first and second bodies 180, 182 which preferably have a hook receivable surface or portion. The surface 172 opposite the hook surface preferably is smooth or lacks hooks elements so as not to catch on any surrounding surfaces. The surface 172 may be defined by a brushed loop surface or covered by a polymer. The securing device 150 as a whole is flexible and capable to conform to the two bodies and movement of the wearer of a corresponding orthopedic device, strap or other bodies upon which the securing device attaches to.

According to the securing device 150 of FIG. 6, the securing device 150 defines first and second areas 176, 178 which may define anchor and head areas, respectively. The first and second areas 176, 178 preferably have approximately the same surface area to provide equal engagement of the first and second bodies. Side areas 157 may exist between the first and second areas 176, 178 that can be used to additionally secure to one of the bodies along with the second area, or be arranged spaced between the first and second bodies. Despite the side areas 157, the bulk of traction on the first and second bodies is created by the first and second areas 176, 178.

The first area 176 defines first and second anchor tabs 154, 156 arranged to clasp opposed surfaces of the first body 180, whereas the second area 178 defines a tab head 152 arranged to grasp a surface of the second body 182. The second anchor tab 156 is bendable toward the first anchor tab 154 so the hook surface of the tabs 154, 156 face one another and are capable of clasping opposed surfaces bearing hook receivable material, such as a soft good formed by or on the first body 180.

The first anchor tab 154 defines a notch 158 between first and second extensions 160, 162 adapted to secure to the first body 174. The notch 158 provides an intuitive reminder that the securing device 150 is adapted to be adjusted from the tab head 152 rather from the first anchor tab 154. However, if adjustment of the first area 176 is required, the extensions 160, 162 can be stripped from the first body 180.

The tab head 152 is the primary portion of the securing device 150 arranged to adjustably secure to the second body 182, and therefore join the first and second bodies. The tab head 152 defines a bullet nose profile having a single surface making it easier to adjust rather than the multiple extensions 160, 162 defined by the first anchor tab 154. The bullet nose likewise obviates sharp edges that may cause any catching on surrounding surfaces.

The first area 176 defines an opening 164 having a profile of the second anchor tab 156, and permits the second anchor tab 156 to bend toward and clasp the first body 180. The second anchor tab 156 bends at a fold line 170 relative to the first anchor tab 154. The second anchor tab 156 defines a bend area 186 adapted to wrap around an edge 184 of the first body. The second anchor tab 156 defines an anchor neck 166 and an anchor head 168 primarily adapted to secure to the surface of the first body. The anchor head 168 preferably flares outwardly from the anchor neck 166 to extend over a greater surface of the first body. The anchor neck 166 extends a distance from the edge of the first body to avoid slippage of the anchor head 168 from the first body, and avoid exerting excessive strain at the edge of the first body.

FIGS. 8A-8E illustrate steps for fitting the wrist brace onto the wearer. First, as shown in FIG. 8A, the wrist brace is loosened by adjusting the strap tab 78 of the main securing device 70 to loosen the laces 72. Next, in FIG. 8B, the hand is inserted into the wrist brace with the thumb being inserted into the thumb hole for proper configuration. The strap tab 78 is then fastened onto the main body panel 12, as shown in FIG. 8C. Next, in reference to FIG. 8D, the securing device 21 is fastened to the main body panel 12. The dorsal stay 66 should be positioned at the midline of the forearm/hand, and can be selectively placed in any of the upper and lower series of pockets according to the anatomy of the wearer's wrist, as shown in FIG. 8E. The palmar stay should be in neutral alignment with the wrist.

When converting the wrist brace from right to left, or left to right, the dorsal and palmar stays are removed and reinserted into opposite stay pockets. The stay pockets are intended to arrange the stays at the midline on the forearm, and this should be flipped over when converting the brace. The securing device is switched over and mounted on the opposite side.

FIGS. 9A and 9B illustrate the wrist brace 10 with the main body panel 12 and the auxiliary securing device 22, as in FIG. 5, in open and closed configurations. As shown in FIG. 9A, the locking part 92 secures to the inner and outer surfaces 107, 108 of the first wing 28 to about the joint 94, and the secure tab 90 extends freely therefrom. Then, in FIG. 9B, the secure tab 90 is brought to the second wing 30, and secures onto the outer surface 108, bringing the first and second sides I, II together at the distal end of the wrist brace. The wearer can subsequently tension the laces 72 by pulling the strap tab 78 away from the first side I, and fasten it to the outer surface 108 of the second side II. An appropriate extension piece 110, such as an elasticized textile, may extend between the first and second edges 16, 18 to eases application by forming a sleeve to insert the wrist and make the wrist brace more comfortable against the skin of the wearer.

Due to the universal and symmetrical configuration of the main body panel, and the main securing device and auxiliary securing device, the wrist brace can be placed on either right or left hands. The direction in which the main securing device secures onto the securing pads varies depending on which hand the brace is worn. Also, because the auxiliary strap can be clamped onto either of the first and second wings, and subsequently secured to the other corresponding wing, the wrist brace can be adapted for either left or right handed use. The various straps and tabs of the brace can be adjusted and trimmed as necessary to accommodate edema and comfort.

Figure 10:
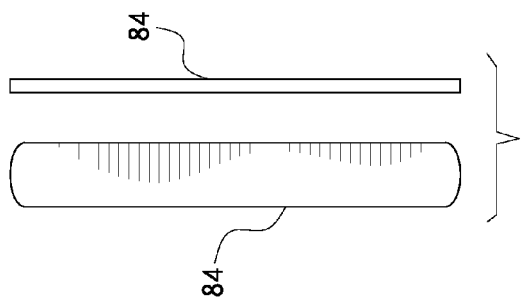
FIG. 10 includes a top plan view and a side view of a thumb stay for the wrist brace of FIG. 1A.

Turning to the stays, FIG. 10 provides an exemplary view of a thumb stay 84 generally flat. The thumb stay is adjustable to allow desired thumb positioning and stability. Each of the stays is substantially rigid, but may be malleable under certain loads to allow for a practitioner to shape the stay for a specific hand. While malleable, it is still preferable that the stay is substantially rigid or at least semi-rigid which the wrist brace is worn.

Figure 11B:
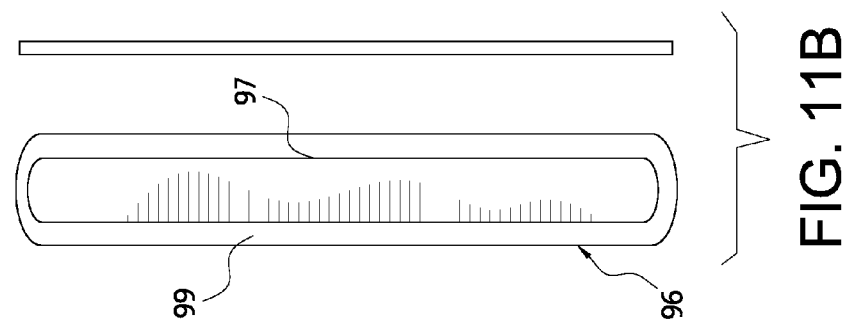
FIG. 11B includes a top plan view and a side view of another embodiment of a dorsal stay.
Figure 11A:
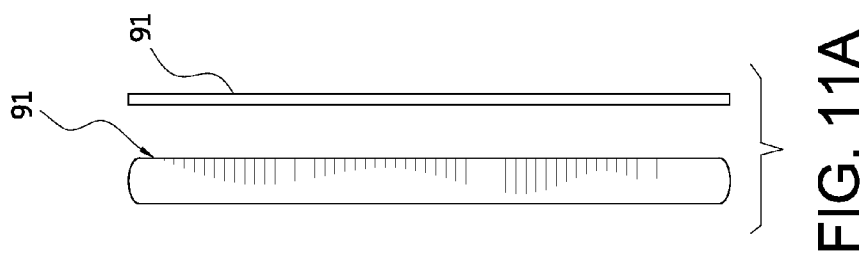
FIG. 11A includes a top plan view and a side view of a dorsal stay for the wrist brace of FIG. 1A.

FIG. 11A is an exemplary embodiment of a dorsal stay 91, having a similar construction to the thumb stay 84, yet at least longer. FIG. 11B provides another exemplary view of a dorsal stay 96 which may be received in either one of the pockets 52, 54, depending on whether the wrist brace is configured for right or left handed use. The dorsal stay 96, in this embodiment, includes a stay insert 97 encapsulated or embedded into a sleeve 99. The sleeve 99 is provided to assure that the stay insert has the same width as the palmar stay, but allows for the stay insert itself to be sized smaller and narrower since it need not be sized as large as the palmar stay. The close resemblance in sizing prevents the dorsal stay from migrating within one of the pockets even if the stay insert is sized smaller than the palmar stay, and allows for the dorsal and palmar stays to be interchangeably inserted into both of the pockets.

The stay insert may be embedded or encapsulated into the sleeve, by molding, welding, stitching or other known methods. The sleeve may be formed from polyurethane which is sufficiently stiff to fill out the pocket, with the much of the strength of the stay coming from the stay insert itself which may be formed from a metal.

FIG. 12 depicts an exemplary view of a palmar stay 98 which defines a longitudinal base portion 100 adapted to the longitudinal support sections 48, 50, a contoured portion 102 with a transition portion 104 located between the base portion 100 and the contoured portion 102, and a substantially flat top portion 106 extending from the contoured portion 102. The contoured portion 102 is generally located in an upper section of the support sections 48, 50, and extends in part into the transition sections 46, 48. The palmar stay 98 is arranged to accommodate the palm of a hand and is received in one of the pockets 52, 54 depending on whether the wrist brace is configured for right or left handed use. The configuration of the palmar stay and the palmar stay pockets on each of the sides of the wrist brace are arranged so the palmar stay is automatically positioned in the correct alignment versus the wrist of the wearer.

Figure 13:
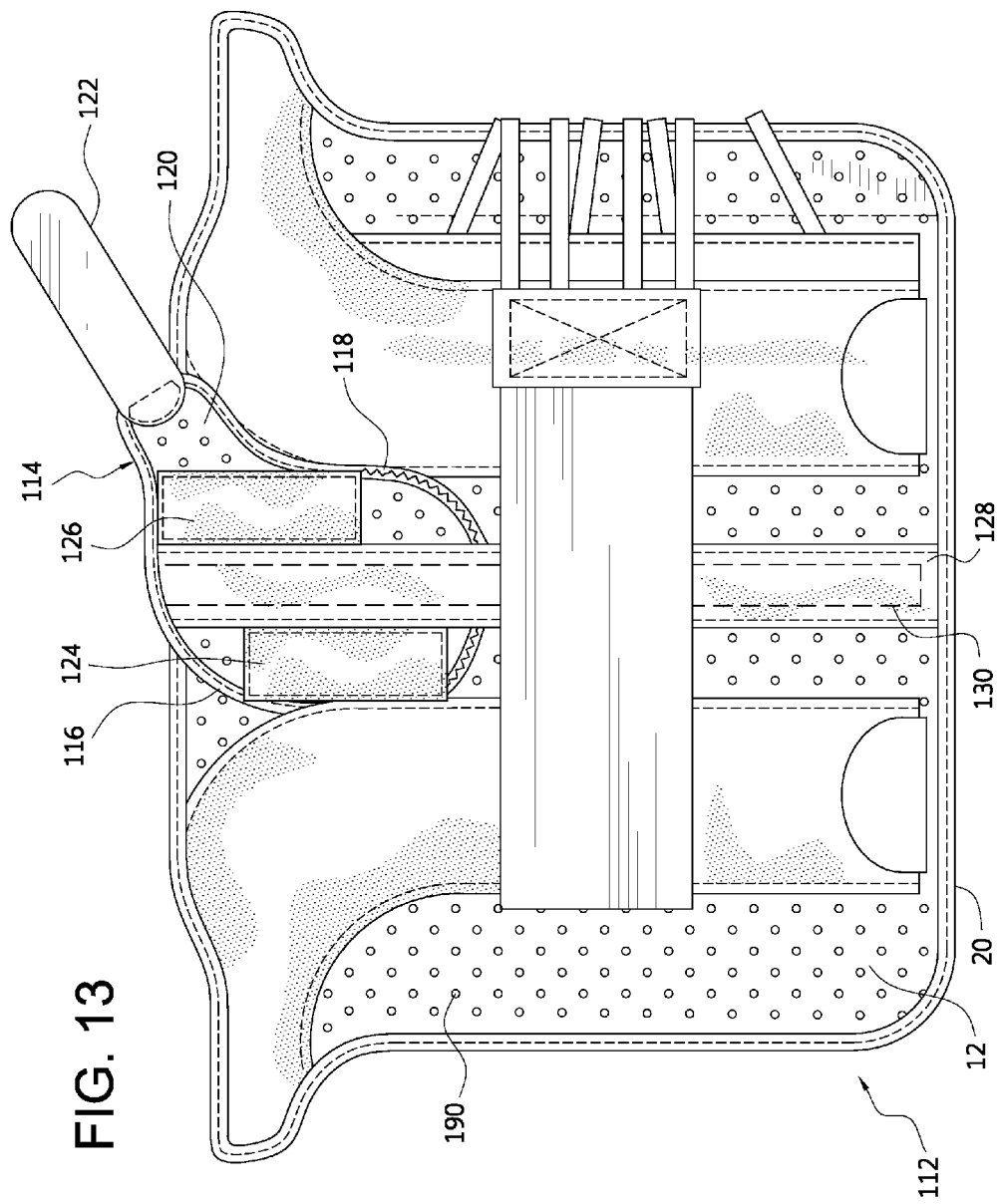
FIG. 13 is a top plan view of a wrist brace embodiment of FIG. 1A having a thumb attachment.

FIG. 13 shows a wrist brace 112 having a thumb attachment 114 which is a variation of the wrist brace 10 according to FIG. 1. In this variation, the wrist brace 112 is constructed in the same manner as in the wrist brace 10, however the wrist brace 112 includes the thumb attachment 114 and may include an elongate thumb stay 130.

The thumb attachment 114 includes first and second side panels 116, 118 generally located adjacent the lower portion or base of the thumb hole or opening 80. The first and second side panels 116, 118 are stitched about the thumb opening 80, and then flexibly extend above the stitching so as to move freely and secure about the thumb. A flap 120 extends from the second panel 118 and carries a thumb secure tab 122. Fastening strips 124, 126 are located along each of the first and second side panels 116, 118, and allow for the thumb secure tab 122 to fasten onto one or both of the fastening strips 124, 126.

The fastening strips 124, 126 are in a staggered relationship so as to facilitate placement of the thumb secure tab 122 about the thumb attachment 114. For example, the fastening strip 124 is located more distal than the fastening strip 126 which allows the thumb attachment to be configured to circumferentially extend about the thumb and be maintained in such configuration.

The thumb stay 130 preferably extends along the longitudinal length of the main body panel, and extends in the main body panel between the first and sides up to the opening. From the opening, the thumb stay 130 includes an outward bend 131 and extends from such bend 131 along the length and within the thumb attachment.

In this variation, the thumb stay 130 is malleable to allow for a practitioner to shape the stay according to the needs of the wearer. The thumb stay 130 may extend along the length of the wrist brace, extending from the lower edge 20 and up to the thumb attachment 114, or may only extend short of the thumb hole 80 and thumb attachment 114. A pad 128 is provided along the longitudinal length of the main body panel, extending from the lower edge to an upper edge of the thumb attachment 114.

Figure 14:
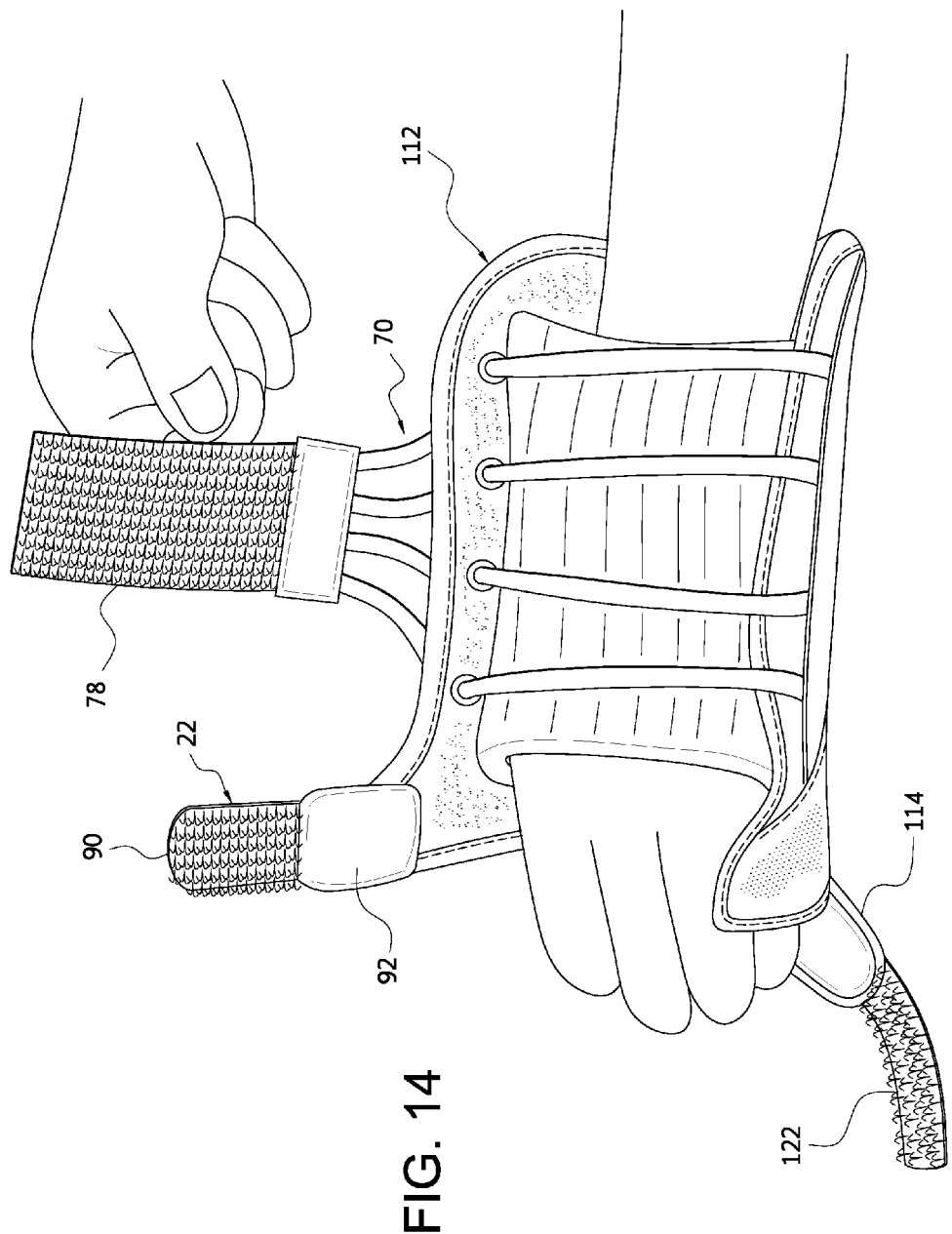
FIG. 14 is a perspective view of the wrist brace of FIG. 13 showing the wrist brace in an open configuration on the wrist of a wearer.

FIGS. 14-16 show how the wrist brace 112 is placed on the hand and wrist of the wearer, with the thumb attachment 114 in an open configuration and the main and auxiliary securing devices 70, 22.

In FIG. 14, the strap tab 78 is in an open configuration and prepared for wrapping about and securing to the main body panel. The locking flaps 92 are fastened to one of the wings and the secure tab 90 is an open configuration prepared for securing to an opposed wing. The thumb attachment 114 is open with the strap secure tab 122 open for securing to the fastening strips.

FIG. 15 shows the thumb attachment 114 as wrapped around the inside of the thumb and about the thumb stay 130. FIG. 16 shows the thumb attachment 114 as having been wrapped about the thumb with its strap secure tab 122 securing to one of the fastening strips 124.

Not necessarily all such objects or advantages may be achieved under any embodiment of the invention. For example, those skilled in the art will recognize that the invention may be embodied or carried out to achieve or optimizes one advantage or group of advantages as taught without achieving other objects or advantages as taught or suggested.

The skilled artisan will recognize the interchangeability of various components from different embodiments described. Besides the variations described, other known equivalents for each feature can be mixed and matched by one of ordinary skill in this art to construct an orthopedic brace under principles of the present invention. Therefore, the embodiments described may be adapted to orthopedic systems for securing, supporting or comforting limbs or other anatomy.

Although this invention has been disclosed in certain preferred embodiments and examples, it therefore will be understood by those skilled in the art that the present invention extends beyond the disclosed embodiments to other alternative embodiments and/or uses of the invention and obvious modifications and equivalents. It is intended that the scope of the present invention disclosed should not be limited by the disclosed embodiments described above, but should be determined only by a fair reading of the claims that follow.

The invention claimed is:

1. A wrist brace comprising:
   a main body panel having first and second sides and a lower edge, the main body having a center axis equally dividing the first and second sides in a longitudinal direction in a flat configuration of the main body panel;
   a first side edge extending parallel in the longitudinal direction relative to and along the first side of the main body panel to the lower edge;
   an upper edge portion extending straight in a transverse direction perpendicular to the longitudinal direction and relative to and along the main body panel and opposed to the lower edge;
   a first wing flaring and extending away from and beyond only the first side edge in the transverse direction directly from the first side edge, and located between the upper edge portion and the first side edge along the main body panel;
   an adjustable auxiliary securing device having an anchor tab removably and directly securable to one of the first and second wings to directly secure a tab head of the adjustable auxiliary securing device to another one of the first and second wings depending on whether the wrist brace is in a right- or left-handed configuration;
   a second side edge extending parallel in longitudinal direction along the second side of the main body panel to the lower edge;
   a second wing flaring so as to extend away from and beyond only the second side edge in the transverse direction directly from the second side edge, and located between the upper edge portion and the second side edge;
   first and second upper contoured edge portions extending directly and obliquely downwardly away from the upper edge portion and extend directly to the first and second wings, respectively;
   wherein the first and second wings define first and second side contoured edge portions, respectively, and which transition obliquely by extending upwardly and outwardly relative to and directly adjacently from the first and second side edges oriented in the longitudinal direction;
   wherein the first and second side contoured edge portions are located between the first and second wings, and the first and second side edges, and extend outwardly away from one another in opposed directions, and from the first and second side edges;
   wherein the first and second wings are symmetrically formed with one another.

2. The wrist brace according to claim 1, wherein the main body panel defines an opening generally located equally between the first and second sides, proximate and adjacent to the upper edge portion such that the main body surrounds an entirety of the opening at an upper end of the wrist brace.

3. The wrist brace according to claim 2, wherein the opening has a generally oval and elongate shape extending along the longitudinal direction.

4. The wrist brace according to claim 2, further comprising a thumb attachment secured to the main body panel about only a lower portion of the opening, the thumb attachment protruding outwardly from the main body panel and having a secure tab adapted to transform the thumb attachment from the flat configuration into a circumferential configuration.

5. The wrist brace according to claim 1, further comprising a plurality of elongate pockets defined along each of the first and second sides in the longitudinal direction.

6. The wrist brace according to claim 5, wherein at least one of the plurality of pockets defines first and second subpocket regions, the first subpocket region extending directly below at least a portion of the second subpocket region.

7. The wrist brace according to claim 6, wherein the second subpocket region has a greater width than the first subpocket region, the second subpocket region is sized and configured to receive a palmar stay and the first subpocket region is sized and configured to receive at least one dorsal stay having a shorter width than the palmar stay.

8. The wrist brace according to claim 1, wherein the the anchor tab has a pair of flaps clamping onto the one of the first and second wings upon which the anchor tab adjustably secures.

9. The wrist brace according to claim 1, further comprising a first securing pad generally following a trajectory of the first wing and the upper edge portion in the transverse direction and following a trajectory of the first side edge in the longitudinal direction.

10. The wrist brace according to claim 1, further comprising a first stay removably located within the main body panel in either the first and second sides.

11. The wrist brace according to claim 1, further comprising at least one pocket defined along one of the first and second sides, the pocket defining first and second subpocket regions, the first subpocket region extending directly below at least a portion of the second subpocket region;
 a first stay arranged to be received by the first subpocket region;
 a second stay arranged to be received by the second subpocket region, the second stay having a different width from a width of the first stay.

12. The wrist brace according to claim 1, further comprising a main securing device having a plurality of laces anchored to the second side of the main body panel, and passing through a plurality of eyelets located on the first side of the main body panel, the main securing device further including a tab carrying the laces and adapted to secure over the main body panel.

13. The wrist brace according to claim 1, wherein an upper edge segment of the first and second wings adjacently extending from the first and second upper contoured edge portions is straight and parallel with the upper edge of the main body panel.

14. A wrist brace comprising:
 a main body panel having first and second wings located at a distal end flaring outwardly from longitudinal and straight first and second side edges, respectively, of the main body panel in a transverse direction of the main body panel and parallel to a straight upper edge portion, the main body panel having symmetrical first and second sides equally divided by a longitudinal axis in a flat configuration of the wrist brace and parallel to the longitudinal axis, the first and second side edges extending only directly adjacent to and between the first and second wings, respectively, and a lower edge of the main body panel, first and second upper contoured edge portions extending directly and obliquely from the upper edge portion and extend directly to the first and second wings, respectively, first and second side contoured edge portions;
 the main body panel defining an opening generally located between the first and second sides and centrally located along the longitudinal axis, proximate and adjacent to the upper edge portion so as to be entirely bordered by the main body panel, the opening having a generally oval and elongate shape extending along longitudinal axis of the main body panel;
 a main securing device is anchored to the first side of the main body panel and detachably attaches to the second side of the main body panel;
 an adjustable auxiliary securing device having an anchor tab removably and directly securable to one of the first and second wings to directly secure a tab head of the adjustable auxiliary securing device to another one of the first and second wings depending on whether the wrist brace is in a right- or left-handed configuration;
 wherein the first and second side contoured edge portions are located between the first and second wings, and the first and second side edges, and extend outwardly away from one another in opposed directions, and from the first and second side edges.

15. The wrist brace according to claim 14, further comprising a first stay removably located within the main body panel in either the first and second sides.

16. The wrist brace according to claim 14, wherein the anchor tab has a pair of flaps clamping onto the one of the first and second wings upon which the anchor tab adjustably secures.

17. The wrist brace according to claim 14, wherein the first and second wings extend transversely relative to an upper portion of the opening, and the main securing device extends from the first side of the main body panel at a location transversely or below relative to a lower portion of the opening, the first and second wings and the main securing device being separated by a distance parallel to the central axis.

18. A wrist brace, comprising:
 a main body panel having a straight upper edge, first and second sides, and a straight lower edge, a center axis equally dividing the first and second sides in a longitudinal direction in a flat configuration of the main body panel;
 a thumb hole centrally located between the first and second sides and formed at an upper end of the wrist brace such that the thumb hole is surrounded by its entirety by the main body panel and defined along the center axis;
 a first side portion extending in the longitudinal direction relative to and along the first side of the main body panel to the lower edge;
 a first upper contoured edge portion extending downwardly and obliquely adjacently from the upper edge in a transverse direction perpendicular to the longitudinal direction and away from and relative to the thumb hole;
 a first wing flaring and extending adjacently away from the first upper contoured edge portion and beyond only the first side portion in the transverse direction relative to the thumb hole, the first wing having a first lower side contoured edge portion extending upwardly directly adjacently from the first side portion;
 a fastening strap secured to the second side of the main body panel, and connecting to the first wing and a second wing;
 a plurality of laces having second ends anchored to the second side of the main body panel and arranged to extend across to the first side of the main body panel to feed through eyelets along the first side to be redirected to the second side of the main body panel;

a second side portion extending in a longitudinal and straight direction relative to and along the second side of the main body panel to the lower edge;

a second upper contoured edge portion extending downwardly and obliquely adjacently from the upper edge in a transverse direction away from and relative to the thumb hole;

a second wing flaring and extending away adjacently from the second upper contoured edge portion and beyond only the second side portion in the transverse direction relative to the thumb hole, the second wing having a second lower side contoured edge portion extending upwardly directly adjacently from the second side portion;

wherein the first lower side contoured edge portion and the second lower side contoured edge portion are defined by the first and second wings, and the first and second side portions, and extend outwardly and away from one another in opposed directions and outwardly relative to the thumb hole;

an adjustable auxiliary securing device having an anchor tab removably and directly securable to one of the first and second wings to directly secure a tab head of the adjustable auxiliary securing device to another one of the first and second wings depending on whether the wrist brace is in a right- or left-handed configuration;

wherein the first and second sides of the main body panel are symmetrical.

19. The wrist brace according to claim 18, wherein the anchor tab has a pair of flaps clamping onto the one of the first and second wings upon which the anchor tab adjustably secures.

20. The wrist brace according to claim 18, wherein the first and second wings extend transversely relative to an upper portion of the thumb hole, and the plurality of laces extend from the first side of the main body panel at a location transversely or below relative to a lower portion of the opening, the first and second wings and the plurality of laces being separated by a distance parallel to the central axis.

* * * * *